United States Patent [19]
Kuhrts

[11] Patent Number: 5,292,518
[45] Date of Patent: * Mar. 8, 1994

[54] PROLONGED-RELEASE DRUG TABLET FORMULATIONS

[75] Inventor: Eric H. Kuhrts, Santa Barbara, Calif.

[73] Assignee: Hauser-Kuhrts, Redwood City, Calif.

[*] Notice: The portion of the term of this patent subsequent to Mar. 17, 2009 has been disclaimed.

[21] Appl. No.: 851,584

[22] Filed: Mar. 16, 1992

Related U.S. Application Data

[63] Continuation-in-part of Ser. No. 440,730, Nov. 22, 1989, Pat. No. 5,096,714.

[51] Int. Cl.⁵ .................. A61K 9/16; A61K 9/22; A61K 47/26; A61K 47/36
[52] U.S. Cl. ................... 424/439; 424/464; 424/465; 424/466; 424/468; 424/469; 424/485; 424/488; 424/489; 424/494; 424/495; 514/356; 514/777; 514/781; 514/960; 514/782
[58] Field of Search ............... 424/439, 466, 464, 468, 424/469, 465, 485, 488, 489, 494, 495

[56] References Cited

U.S. PATENT DOCUMENTS

| | | | |
|---|---|---|---|
| 3,065,143 | 11/1962 | Christenson et al. | 424/468 |
| 3,870,790 | 3/1975 | Lowey et al. | 424/19 |
| 4,172,120 | 10/1979 | Todd et al. | 424/465 |
| 4,226,849 | 10/1980 | Schor | 424/19 |
| 4,357,469 | 11/1982 | Schor | 536/91 |
| 4,369,172 | 1/1983 | Schor et al. | 424/19 |
| 4,389,393 | 6/1983 | Schor et al. | 424/19 |
| 4,540,566 | 9/1985 | Davis et al. | 424/22 |
| 4,747,881 | 5/1988 | Shaw et al. | 106/209 |
| 4,790,991 | 12/1988 | Shaw et al. | 424/441 |
| 4,795,327 | 1/1989 | Gaylord et al. | 424/468 |
| 4,818,539 | 4/1989 | Shaw et al. | 424/441 |
| 4,824,672 | 4/1989 | Day et al. | 424/195.1 |
| 4,844,905 | 7/1989 | Ichikawa et al. | 424/466 |
| 4,849,229 | 7/1989 | Gaylord et al. | 424/468 |
| 5,023,245 | 6/1991 | Kuhrts | 514/54 |
| 5,047,248 | 9/1991 | Calanchi et al. | 424/468 |
| 5,096,714 | 3/1992 | Kuhrts | 424/466 |

FOREIGN PATENT DOCUMENTS

| | | |
|---|---|---|
| 0080673 | 6/1973 | European Pat. Off. . |
| 2030583 | 5/1979 | United Kingdom . |

OTHER PUBLICATIONS

Council Report, *"Dietary Fiber and Health,"* Journal of the American Medical Association, Jul. 28, 1989, vol. 262, No. 4, pp. 542–546.

*Primary Examiner*—Thurman K. Page
*Assistant Examiner*—James M. Spear
*Attorney, Agent, or Firm*—Bertram I. Rowland

[57] ABSTRACT

A prolonged-release unit dosage formulation or pharmaceutical composition, preferably in tablet form, is described. The composition consists essentially of a gel-forming dietary fiber, a biologically-absorbable drug or other active therapeutic agent, and a disintegrant, namely, a mineral salt which releases a physiologically-acceptable gas upon ingestion, preferably carbon dioxide, e.g., a mineral carbonate or bicarbonate, and advantageously dextrose or like soluble sugar. A physiologically-acceptable acid may optionally be included in the composition to further facilitate disintegration. The dietary fiber-containing composition, when compressed into a tablet together with the drug and the specific disintegrants, provides a unique and efficient prolonged-action drug-delivery system.

69 Claims, No Drawings

PROLONGED-RELEASE DRUG TABLET FORMULATIONS

The present invention is a continuation-in-part of my prior-filed application, Ser. No. 440,730, filed on Nov. 22, 1989, now U.S. Pat. No. 5,096,714.

BACKGROUND OF THE INVENTION

1. Field of the Invention and Prior Art

The present invention relates to novel prolonged release formulations or compositions, e.g., tablet, granule, lozenge, capsule, or like formulations, containing a gel-forming dietary fiber and a drug or other active therapeutic agent plus certain essential disintegrants.

Many drugs and vitamins must be released in a uniform and/or continuous manner over a period of time. Water-soluble vitamins, for example, unless placed into a time-release form, are almost immediately released into the blood stream once they dissolve in the stomach. Aspirin is frequently coated to minimize gastric upset and release the drug over a period of time. Sustained-release dosage forms also avoid the necessity of frequent administration of the drug while, at the same time, achieving a desired blood level of active ingredient.

Various cellulose derivatives have been used to provide rapid disintegration of tablets, such as in U.S. Pat. No. 3,266,992, which describes the use of methylcellulose, sodium carboxymethylcellulose and hydroxyethylcellulose for such purpose. However, in contrast, hydroxypropylmethylcellulose in enteric coatings has been disclosed in U.S. Pat. No. 2,887,440 to prevent disintegration of a tablet core and delay release of the active ingredients.

U.S. Pat. No. 3,870,790 discloses a method of preparing a long-acting buccal composition for admini-stering a therapeutic agent using an effective amount of hydroxypropylmethylcellulose which has been subjected to controlled humidity. Other processes for treating cellulose derivatives are described in U.S. Pat. Nos. 4,226,849, 4,357,469, 4,369,172, 4,389,393, 4,540,566, 4,795,327, and 4,849,229, the treated cellulose derivatives then being used in a solid drug dosage unit form to produce a controlled and prolonged release pattern of a drug upon administration thereof.

For purposes of definition in this Specification, the term "dietary fiber" is defined as "remnants of plant cells resistant to hydrolysis by the alimentary enzymes of man, the group of substances that remain in the ileum but are partly hydrolyzed by bacteria in the colon", according to JAMA 262, No. 4, 542,546 (Jul. 28, 1989) in the Council Report entitled "Dietary Fiber and Health", at page 542. This article, moreover, gives considerable information as to what constitutes a "dietary fiber" and is accordingly incorporated herein by reference.

Gel-forming dietary fibers include mucilages, plant gums, pectins or pectic substances, and lignin, all of which are endogenous compounds of plant materials which are resistant to digestion by enzymes in the monogastric stomach or small intestine. Chemically, nearly all of these plant materials are carbohydrates composed of repeating monosaccharide (sugar) units. Disaccharides have two sugar units, oligosaccharides three to twelve, and polysaccharides may contain a million or more. The water-soluble fractions of these substances form gels in the stomach and intestinal tract and are known to lower serum cholesterol.

Gums and mucilages have no common structure but are polysaccharides containing several sugars with alternating monomer structures and may or may not contain uranic acids. There are many gums found in plants and cereal grains. Guar and locust bean gums are galactomannans, whereas gum arabic is an acidic polymer of galactose and rhamnose. Oat and barley contain gums, but are not practical for use in the present application because of the low percentage of active gum per weight volume. Most of the gums in the present application are effective at much lower dosages. Suitable gums include, inter alia, besides guar gum, the following: locust bean gum, acacia gum, gum arabic, xanthan gum, carrageenan gum, karaya gum, tragacanth gum, and ghatti gum.

Pectin substances or pectins are mixtures of polysaccharides of partially methylated and 1,4-D galacturonic acid units with side chains containing arabinose, galactose, xylose, and rhamnose. They are contained in many fruits and vegetables as well as other plants.

Other suitable gel-forming dietary fibers include psyllium husks, algal polysaccharides, glucomannan, and agar, to name a few. Lignin is a non-carbohydrate polymer of aromatic plant alcohols comprising oxygenated phenylpropane units. As a plant matures, more lignin is produced, which acts as a sort of cement as it hardens and holds together other plant cell wall constituents. Lignin passes through the digestive tract with very little change.

As already mentioned, a recent review of dietary fiber which mentions these substances is contained in the following reference: Dietary Fiber and Health, JAMA 262: No. 4, 542–546 (1989), from the Council on Scientific Affairs, American Medical Association.

Some gel-forming fibers such as guar gum are used as binders and disintegrators for compressed tablets, but at fairly low levels. At higher levels, these gel-forming fibers and gums are known not to dissolve properly when compressed into tablets.

Various unsuccessful attempts have been made to solve the problem of improper and incomplete dissolution of guar gum tablets. EPA 0080673 describes these problems in detail, and discloses the use of 5 to 30% of highly-dispersed silica gel in guar tablets. Normally used tablet disintegrants or additives such as polyvinylpyrrolidone (crosslinking agent), sodium carboxymethyl-starch, cornstarch, microcrystalline cellulose, and so on, do not lead to satisfactory results. Hard tablets are produced which do not swell properly, and which form an impenetrable layer of gel around a powder core which may pass through the gastrointestinal tract undissolved.

U.S. Pat. No. 4,824,672 describes the use of mineral carbonates to enhance dispersion of gel-forming dietary fibers in orally-administrable pharmaceutical compositions for use in reducing serum cholesterol levels. Such compositions have proved to be very effective in use for their intended purpose, but do not provide a satisfactory matrix for providing a prolonged-release unit dosage formulation of a biologically-absorbable therapeutic agent or drug.

The foregoing EPA 00808673 mentions the employment of citric acid with guar gum tablets. The citric acid and sweeteners were used, according to that disclosure, to improve the acceptability of the tablets if they were to be chewed. Accordingly, the citric acid was there used only to provide flavor and an aromatic quality to the product.

It is apparent that the prior art has not provided such formulations did not contain any mineral carbonate or bicarbonate and, moreover, when a carboxylic acid such as citric acid was employed in the compositions of that invention, "the acid is coated with 1 to 20% of a water-repellent agent based on the weight of the acid", reportedly to provide increased storage stability of the product.

It is apparent that the prior art has not provided any suitable prolonged-release unit dosage formulation for the prolonged release of an effective dose of a biologically-absorbable therapeutic agent or drug, much less such a prolonged-release unit dosage formulation which employs or embodies a gel-forming dietary fiber as an essential part of the matrix, fundamentally because of the fact that the swelling and balling and plug formation of such gel-forming dietary fibers has heretofore been considered an insurmountable disadvantage, insofar as the acid of the stomach does not readily or uniformly dissolve dietary fiber formulations, especially when in unit dosage form such as a tablet, granule, capsule, lozenge, or the like, for which reason release of any therapeutic agent or drug which may have been combined therewith was unpredict-able and non-uniform and generally insufficiently rapid to cause or permit release of all of the drug or other therapeutic agent content thereof while the unit dosage formulation was present in the gastrointestinal tract.

According to the present invention, however, excellent prolonged-release unit dosage formulations are provided, which consist essentially of an effective dose of the selected biologically-absorbable therapeutic agent or drug, a gel-forming dietary fiber, and optionally a physiologically-acceptable edible acid, preferably a food-grade organic acid or phosphoric acid, and a mineral salt which releases a physiologically-acceptable gas upon ingestion, preferably a mineral carbonate or bicarbonate which releases carbon dioxide upon ingestion. The physiologically-acceptable acid is not necessary to carry out the present invention, although it can be present to assist in providing an improved hydration rate and help to open up the tablet or other selected oral unit-dosage form involved when a quicker release of the drug is desired. According to the invention, when a biological liquid, such as stomach acid, begins to penetrate or wick into the prolonged-release unit dosage formulation, it dissolves mineral salt present therein, which reacts to cause a rapid evolution of gas, e.g., carbon dioxide. This rapid evolution of gas breaks up the prolonged-release unit dosage form, e.g., tablet, granule, capsule, lozenge, or the like, before a surface layer of gel can form around the unit dosage form, especially a tablet, from the normal reaction of the gel-forming dietary fiber, which surface layer of gel would seal the unit dosage form off from further hydration and disintegration. In another embodiment of the present invention, it may be necessary to have a physiologically-acceptable edible acid with the mineral salt to release a physiologically-acceptable gas upon ingestion. The acid would be located inside the tablet, granule, capsule, lozenge, or the like, or dispersed throughout the tablet granule, capsule, lozenge, or other unit dosage form, to increase the speed of hydration of the drug or other therapeutic agent contained in the unit dosage formulation.

According to the invention, the gel produced by the gel-forming dietary fiber modulates the release of the drug, but does not prevent the drug from being biologically absorbed, inhibition of disintegration by formation of a gel coating around the unit dosage formulation by the gel-forming dietary fiber being prevented by the evolution of a physiologically acceptable gas by virtue of the action of the mineral salt within the unit dosage formulation upon contact with biological fluids, e.g., those of the gastrointestinal tract.

It is an object of the invention to provide novel and advantageous prolonged-release unit dosage formulation and a method for prolonging the release of a drug or other active therapeutic agent upon administration to a human being involving the employment of such improved and advantageous prolonged release unit dosage formulation of the invention. Another object of the invention is to provide such formulation and method which involve the employment of a prolonged-release unit dosage formulation consisting essentially of an effective dose of a biologically-absorbable drug or other therapeutic agent, a gel-forming dietary fiber, and a mineral salt which releases a physiologically- acceptable gas upon ingestion. A further object of the invention is to optionally provide the above composition along with a physiologically acceptable acid. A further object of the invention is the provision of such formulation and method wherein the disadvantageous characteristics of the gel-forming dietary fiber matrix are offset by the inclusion of a mineral salt which releases a physiologically-acceptable gas upon ingestion, preferably a mineral carbonate or bicarbonate which releases carbon dioxide upon ingestion and to optionally include a physiologically-acceptable acid to facilitate the release of the gas. Still an additional object is the provision of such a formulation and method wherein the unit dosage formulation also contains a soluble sugar, which greatly enhances the controllable disintegration of the unit dosage formulation upon ingestion in addition to providing a more generally acceptable flavor. Still other objects will be apparent to one skilled in the art and additional objects will become obvious as this specification proceeds.

SUMMARY OF THE INVENTION

In accordance with the present invention, a prolonged-release unit dosage formulation or composition is provided which prolongs the release of a drug or other active therapeutic agent upon administration to a human being. The formulation consists essentially of an effective dose of a biologically-absorbable drug or other therapeutic agent, a gel-forming dietary fiber, and a mineral salt, this composition releasing a physiologically-acceptable gas upon ingestion. The mineral salt may be any mineral carbonate or bicarbonate, such as calcium carbonate, magnesium carbonate, magnesium bicarbonate, sodium carbonate, sodium bicarbonate, potassium carbonate, or potassium bicarbonate. The physiologically-acceptable gas released upon ingestion when the composition comes in contact with the biological fluids of the stomach, is carbon dioxide. Further, the formulation and method may contain a soluble sugar, which greatly enhances the controllable disintegration of the unit dosage formulation upon ingestion, in addition to providing a more generally acceptable flavor.

Further, in another embodiment of the present invention, a physiologically-acceptable edible acid may be added to the formulation. The acid is added to facilitate faster and greater release of the physiologically-acceptable gas upon ingestion. The acid is preferably a food-grade organic acid or phosphoric acid.

Other objects, features, and advantages of the invention will become apparent from a consideration of the following detailed description and from the accompanying examples.

THE INVENTION

It has now been discovered that unit dosage formulations, especially tablets, consisting essentially of a gel-forming fiber, especially guar gum, and a drug, vitamin, dietary food supplement, or other active therapeutic agent, produce a unique, prolonged action and advantageous delivery system, when combined with certain essential disintegrants, as hereinafter described. The problem which needed to be overcome was a proper disintegration of the tablet, so that the gel produced by the fiber could modulate the release of the drug. Otherwise a solid tablet containing the drug would start to hydrate, but stop abruptly when a film of gel sealed off the rest of the tablet and inhibited its full disintegration, thereby preventing release of the active drug or other therapeutic agent. The discovery of the present invention is therefore twofold. It provides both a delivery system for therapeutic compounds wherein the delivery vehicle is a gel-forming dietary fiber which, when dissolved in the fluids of the gastrointestinal tract, forms a gel which modulates but does not stop the release of the therapeutic agent, and a solution to the problem of a proper and complete dissolution of tablets in the stomach with release of the drug or other active therapeutic agent.

This is effected, according to the present invention, by the inclusion, in the unit dosage formulation of the invention, of a mineral salt which releases a physiologically-acceptable gas upon ingestion and while the unit dosage formulation is in the gastrointestinal tract, which gas penetrates and modulates the film of gel produced from the gel-forming dietary fiber and thus assists in the proper disintegration of the unit dosage form and the proper dissolution of all of the drug or other therapeutic agent present in the unit dosage formulation. A physiologically-acceptable acid may be included to further increase the production of the physiologically-acceptable gas, although the inclusion of the acid is not a necessity. The unit dosage form of the invention becomes activated upon contact with biological fluids, i.e., body fluids, e.g., saliva, gastrointestinal fluids, or rectal fluids, and dissolves slowly, with the internally-contained acid and mineral salt cooperating to mechanically disperse the fiber in a slow and prolonged manner as it hydrates, the gas released by the mineral salt and organic or other acid, if present, cooperating to mechanically disperse the fiber in a slow and prolonged manner as it hydrates, the gas released by the mineral salt assisting in the slow disintegration of the unit dosage form.

The present invention preferably employs a mineral carbonate or bicarbonate, an optional physiologically-acceptable organic acid or phosphoric acid, and preferably also a soluble sugar such as dextrose, all of which aid in the proper disintegration and dissolution of the tablet.

The Physiologically-Acceptable Acid - Optional

As physiologically-acceptable acid may be employed, although it is not a necessary ingredient in the present invention. Any non-toxic and preferably edible acid such as citric, malic, succinic, ascorbic, fumaric, phosphoric, tartaric, gluconic, acetic, tannic, lactic, glycolic, or the like may be used. Food-grade organic acids are preferred and, of organic food-grade acids, citric, tartaric, and malic are preferred due to their introduction of a definite citrus, grape and apple flavor into the composition, respectively.

The Gel-Forming Dietary Fiber

According to the invention, any of the foregoing enumerated gel-forming dietary fibers may be employed, with gums such as guar gum and the like and psyllium seed husks in powdered form being preferred, but pectin or a pectic substance, algal polysaccharides, glucomannan, agar, lignin, or the like, or combinations thereof, may generally be employed with essentially the same results.

The Mineral Salt

According to the invention, any mineral salt which releases a physiologically-acceptable gas upon ingestion may be employed. Such gas released is preferably carbon dioxide and the mineral salt is preferably a mineral carbonate or bicarbonate, with calcium carbonate, magnesium carbonate, magnesium bicarbonate, sodium carbonate, and sodium bicarbonate, as well as the corresponding potassium carbonate and bicarbonate, being preferred.

Soluble Sugar

As the optional but most preferred soluble sugar employed to assist disintegration according to the invention any of the following representative sugars may be employed: Dextrose, sucrose, glucose, xylose, ribose, mannose, galactose, fructose, maltose, partially hydrolyzed starch, corn syrup solids, sugar alcohols such as sorbitol, xylitol, mannitol, and the like, with dextrose, xylose, and fructose being preferred.

Tableting Pressures and Procedure

According to the invention, in producing tablets, usual tableting procedure and practice is employed, with pressures ranging from about 4,000 to about 10,000 pounds per square inch being preferred. Due to the fact that the gel-forming dietary fibers become closely compacted and even more difficult to disintegrate pressures above about 10,000 pounds per inch are employed care must be taken that the possibility of disintegration of the tablet is not impaired. To this end, cellulose flocked granules, microcrystalline cellulose, plain or chemically-modified starch, lactose, dextrose, mannitol, carboxymethylcellulose, methylcellulose, lubricants such as magnesium stearate or polyethylene glycols, or mineral excipients such as dicalcium phosphate, silicon dioxide, talc, and the like may be included singly or in combination in any desired ratio as a blend, but in any event only to the extent necessary and for the purpose of providing a tablet hardness sufficient for maximum tablet stability but not so great that the disintegration rate in water or gastric fluid is disadvantageously affected.

Ranges of Ingredients

According to the invention, the range for the gel-forming dietary fiber comprising an essential part of the prolonged-release matrix of the present invention should be about 10% to 85% by weight, preferably about 50% by weight; the range of the optional physiologically-acceptable edible acid should be 0% to about 50% by weight, preferably about 5% by weight; the range for the mineral salt should be about 5% to about 75% by weight, preferably about 15% by weight. The gel-forming fiber to drug weight ratio should be between about 1,000:0.5 and 1:1.5. Therapeutic agents which are employed in microgram dosages fall at the higher end of the range and therapeutic agents which require relatively larger amounts for a therapeutically-effective dose fall at the lower ends of the range, as will be readily understood and as illustrated by the Examples herein. When present, the soluble sugar is preferably present in an amount between about 1 and about 30% by weight, preferably between about 3 and about 12% by weight.

DETAILED DESCRIPTION OF PREFERRED EMBODIMENTS

The following Examples are given to illustrate the compositions and method of the present invention, but are not to be construed as limiting.

Example 1

Tablets were made according to the following formula:

| | |
|---|---|
| Guar Gum | 400 mg |
| Aspirin | 200 mg |
| Calcium Carbonate | 100 mg |
| Dextrose | 50 mg |
| Citric Acid | 25 mg |
| Microcrystalline-Cellulose (MCC) | 25 mg |

The citric acid and calcium carbonate act to mechanically disintegrate the guar gum fiber so that it forms a sphere or plug of hydrated gel which coats the aspirin and from which the aspirin slowly leaches as the gel hydrates and passes through the gastrointestinal tract. The gel-forming fiber also assists in minimizing the caustic effect of the aspirin when it comes into full contact with the stomach, because the "gel plug" or sphere of fiber-gel insulates the aspirin as well as modulates its release.

Other fibers, drugs, mineral salts, acids, and soluble sugars may obviously replace those employed in the foregoing Example.

Example 2

Tablets were made by compression at usual pressures of 4,000 to 10,000 pounds per square inch according to the following formula:

| | |
|---|---|
| Locust Bean Gum | 150 mg |
| Acacia Gum | 50 mg |
| Karaya Gum | 100 mg |
| Tragacanth Gum | 50 mg |
| Carrageenan | 50 mg |
| Vitamin C | 250 mg |
| Calcium Carbonate | 100 mg |
| Dextrose | 25 mg |
| Citric Acid | 25 mg |
| Microcrystalline-Cellulose | 25 mg |
| Polyvinylpyrrolidone (crosslinked)-(Povidone TM) | 15 mg |

Other fibers, drugs, mineral salts, acids, and soluble sugars may obviously replace those employed in the foregoing Example.

Example 3

| Stimulant tablet | |
|---|---|
| Guar Gum | 500 mg |
| Caffeine | 100 mg |
| Calcium Carbonate | 200 mg |
| Citric Acid | 75 mg |
| Lactose (Anhydrous) | 50 mg |
| Microcrystalline-Cellulose (MCC) | 25 mg |

Other fibers, drugs, mineral salts, acids, and soluble sugars may obviously replace those employed in the foregoing Example.

Example 4

| Weight-Loss tablet | |
|---|---|
| (Appetite Suppressant) | |
| Guar Gum | 500 mg |
| Phenylpropanolamine base | 5 mg |
| Calcium Carbonate | 200 mg |
| Citric Acid | 75 mg |
| Dextrose | 50 mg |
| Microcrystalline-Cellulose (MCC) | 30 mg |

The Guar Gum expands 3 to 4 times its original size in the stomach, and gives the subject a full feeling, while the phenylpropanolamine tends to shut off the, hunger signal in the brain. These two principle ingredients work together to produce a dual action on the two primary components of a weight loss product, satiety and hunger, while the guar gum also serves to modulate the absorption of the phenylpropanolamine, prolonging its action.

Other fibers, drugs, mineral salts, acids, and soluble sugars may obviously replace those employed in the foregoing Example.

Example 5

Tablets are made according to the following formula:

| | |
|---|---|
| Psyllium seed husks-powdered | 500 mg |
| Niacin | 100 mg |
| Calcium carbonate | 150 mg |
| Dextrose | 50 mg |
| Citric acid | 25 mg |
| Microcrystalline cellulose (Avicel-TM) | 25 mg |

The citric acid and calcium carbonate act to mechanically disperse the gel-forming psyllium fiber which acts as a drug delivery system for the niacin. The psyllium fiber also serves to coat the niacin, minimizing its acidic effect on the stomach lining and intestines.

In the foregoing formulation, some or all of the psyllium seed husk powder may be replaced by another gel-forming dietary fiber, e.g., guar gum or one or more of the gums used in Example 6, pectin or a pectic substance, algal polysaccharides, glucomannan, agar, lignin, or the like, or combinations thereof, with essentially the same result.

Other fibers, drugs, mineral salts, acids, and soluble sugars may obviously replace those employed in the foregoing Example.

Example 6

Tablets are made according to the following formula:

| | |
|---|---|
| Locust bean gum | 100 mg |
| Acacia gum | 100 mg |
| Gum arabic | 100 mg |
| Xanthan gum | 100 mg |
| Karaya gum | 50 mg |
| Tragacanth gum | 50 mg |
| Niacin | 100 mg |
| Calcium carbonate | 150 mg |
| Dextrose | 50 mg |
| Citric Acid | 25 mg |
| Microcrystalline cellulose (Avicel ™) | 25 mg |

In the foregoing formulation, one or more of the gums may be replaced by another gel-forming dietary fiber, e.g., psyllium seed husks, pectin or a pectic substance, algal polysaccharides, glucomannan, agar, lignin, or the like, or combinations thereof, with essentially the same result. These tablets, as well as those of Example 6, are found to be effective in lowering cholesterol levels at effective doses of niacin without the usual side effects of flushing, itching, and irritation.

Other fibers, drugs, mineral salts, acids, and soluble sugars may obviously replace those employed in the foregoing Example.

Example 7

A niacin granulate is produced in a fluid bed granulator (Glatt Air Techniques, Ramsey, N.J.). The niacin is first sprayed with NaCMC (Sodium Carboxy-methylcellulose) at 7.5% solids in solution level, and 3% by weight volume percentage. While still in the fluid bed granulators the coated niacin is then sprayed with Surelease (TM) (Colorcon, West Point, Pa.), an ethyl cellulose preparation, at 15% solids in solution and 2% by weight volume percentage.

Prepare 95% Niacin Granulation

In granulator bowl - Niacin powder.

In solution - Spray first with NaCMC, 7.5% solids in solution, 3% by weight volume percentage. Spray second with Surelease (TM) (ethyl cellulose) 15% solids, 2% by weight volume percentage.

The 95% niacin granulate is then used in the following formula:

| Each Tablet Contains | |
|---|---|
| Psyllium husk powder | 600 mg |
| Niacin granulate (95%) | 160 mg |
| Calcium-carbonate | 100 mg |
| Citric Acid | 25 mg |
| Microcrystalline cellulose (Avicel'") | 25 mg |

In the foregoing formulation, some or all of the 10 psyllium seed husk powder may be replaced by another gel-forming dietary fiber, e.g., guar gum or one or more of the gums used in Example 6, pectin or a pectic substance, algal polysaccharides, glucomannan, agar, lignin, or the like, or combinations thereof, with essentially the same result.

Other cellulose coatings may replace those used for preparation of the coated niacin granulate in the foregoing.

A much higher dose of niacin is found to be possible by granulating the niacin before tableting so that it is released more slowly. A subject can take two tablets of the above formula with virtually no side effects such as the severe flushing, itching, or gastric distress produced by normal niacin.

The tablet ingredients may also be formed into granules, if desired, and then may be taken alone, without tableting, if desired, in effective dosages, but this is generally less convenient from the standpoint of the user and less advantageous from the standpoint of prolonged time-release effect upon ingestion.

Dextrose or other soluble sugar may also be present in an amount up to about 100 mg if desired, to further assist in the tablets' disintegration upon ingestion.

Example 8

| A capsule example is: | |
|---|---|
| Guar Gum | 500 mg |
| Magnesium Carbonate | 80 mg |
| Niacin | 80 mg |
| Citric Acid (fine powder) | 10 mg |

Other fibers, drugs, mineral salts, and acids may obviously replace those employed in the foregoing Example.

Example 9

| Minimum Ratio Example (600:1) (small amount of drug) | |
|---|---|
| Guar Gum | 300 mg |
| Vitamin B-12 | 500 mg |
| Calcium Carbonate | 100 mg |
| Citric Acid | 50 mg |
| Dextrose | 100 mg |
| MCC | 25 mg |

Other fibers, drugs, mineral salts, and soluble sugars may obviously replace those employed in the foregoing Example.

Example 10

| Maximum Ratio Example (1:2) (large amount of drug) Each tablet contains: | |
|---|---|
| Guar Gum | 350 mg |
| Ibuprofen | 700 mg |
| Calcium Carbonate | 50 mg |
| Citric Acid | 50 mg |
| Dextrose | 50 mg |
| MCC | 25 mg |

Other fibers, drugs, mineral salts, and soluble sugars may obviously replace those employed in the foregoing Example.

Example 11

| Longer Controlled Release Tablet | |
|---|---|
| Guar Gum | 500 mg |
| Niacin | 200 mg |
| Calcium Carbonate | 200 mg |
| Microcrystalline Cellulose | 150 mg |
| Dextrose | 50 mg |
| Magnesium Oxide | 25 mg |

| -continued |  |
| --- | --- |
| Longer Controlled Release Tablet | |
| Silicon Dioxide | 15 mg |
| Magnesium Stearate | 15 mg |

Other fibers, drugs, mineral salts, acids, and soluble sugars may obviously replace those employed in the foregoing Example. A physiologically-acceptable acid may be added to aid the drug release.

Example 12

Pharmacological Evaluation Dissolution Test

The tablets from Example 2 are dissolved in a gastric simulator dissolution apparatus at 0.1 N HCl and are observed to take on the appearance of "cotton plugs" or balls of fiber-gel from which the Vitamin C is slowly released. Samples are taken from each vessel at 1, 4, and 6 hours and the Vitamin C content from each is analyzed. The results confirm that the Vitamin C is being slowly released over time from the fiber-gel matrix. Similar tests on other products of the invention likewise confirm the steady prolonged and efficient release of the drug or other therapeutic agent over a prolonged period but with ultimate release of substantially all of the active ingredient within the gastrointestinal tract.

Drugs or Therapeutic Agents

Among drugs or therapeutic agents which maybe incorporated according to this invention, but to which it should not be limited, are:
a. Antipyretics and analgesics such as acetaminophen, aspirin and ibuprofen
b. Appetite suppressants such as phenylpropanol-amine hydrochloride and caffeine
c. Potassium, KCl, or another mineral supplement
d. Vitamin C
e. Vitamin B-12
f. Antihypercholesterolemics, and especially Niacin
g. Antitussives, such as destromethorphan, dextromethorphan hydrobromide, noscapine, carbetapentane citrate, and chlophedianol hydrochloride.
h. Antihistamines, such as chlorpheniramine maleate, phenindamine tartrate, pyrilamine maleate, doxylamine succinate, and phenyl-toloxamine citrate.
i. Decongestants, such as phenylephrine hydro-chloride, phenylpropanolamine hydrochloride, pseudoephedrine hydrochloride, and ephedrine.

Preferred particular drugs, minerals, or vitamins, for which the present delivery system is ideally suited include: Niacin, Vitamin B-12, Potassium Chloride, Vitamin C, Aspirin, Caffeine, Phenylpropanolamine hydrochloride, Ibuprofen, Pseudoephedrine, Nitroglycerin, and Gemfibrozil.

The active ingredient can be any type of medication which acts systemically and which can be administered orally to transmit the active therapeutic agent into the gastrointestinal tract and into the bloodstream in therapeutically-effective levels without early excessive peak concentrations, without being inactivated by physiological fluids, and without passing unchanged through the body of the patient or subject by being excreted unabsorbed. Alternatively, the active ingredient can be any type of medication which acts through the buccal tissues of the mouth to transmit the active ingredient directly into the bloodstream, thus bypassing both any possible first pass liver metabolism and/or the gastric and intestinal fluids, which often have an adverse inactivating or destructive action on the active ingredient unless it is specially protected against such fluids as by means of an enteric coating or the like. The active ingredient can also be a type of medication which can be transmitted into the blood circulation through the rectal tissues.

Representative active therapeutic agents include antacids, anti-inflammatory substances, coronary dilators, cerebraldilators, vasodilators, antibacterials, psychotropics, antimanics, stimulants, anti-histamines, laxatives, decongestants, vitamins, and the like. However, it is to be understood that the invention is also applicable to sublingual lozenges, suppositories, capsules and compressed tablets, the latter being intended to be swallowed in unit dosage form and which, upon ingestion according to a prescribed regimen, give slow and regular release of active therapeutic agent without an initial dumping of a fixed percentage in the intestinal tract while being protected against normally-inactivating gastric fluids, whether administered for therapeutic, preventive, or dietary purposes, and whether employed in human or veterinary therapy.

It is therefore seen that the present invention provides a unique prolonged-release dosage formulation, especially a tablet, consisting of the following as essential ingredients: an effective dose of a biologically-absorbable drug or other therapeutic agent, a gel-forming dietary fiber, such as guar gum, an optional physiologically-acceptable acid, especially a food-grade organic acid or phosphoric acid, a mineral salt which releases a physiologically-acceptable gas upon ingestion, preferably a mineral carbonate or bicarbonate, and advantageously dextrose or another soluble sugar as a further disintegrant, and a method of prolonging the release of a drug or other active therapeutic agent upon administration to a living animal body, e.g., a human being or other animal, by employment of such a prolonged-release pharmaceutical, therapeutic, or dietary composition, all having the unpredictable and highly advantageous characteristics and effects as more fully set forth in the foregoing.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

What is claimed is:

1. A solid prolonged-release oral unit dosage composition for oral administration and ingestion in solid form, and intended to be swallowed as such, which consists essentially of a solid admixture of an effective dose of a biologically-absorbable therapeutic agent or drug, a gel-forming dietary fiber, and a mineral salt which releases a physiologically-acceptable gas upon ingestion, wherein the combination of the fiber and salt provides prolonged but effective release of the drug or therapeutic agent upon oral ingestion and exposure of the solid composition to biological fluids.

2. The composition of claim 1, wherein the gel-forming dietary fiber comprises about 10% to about 85% by weight, the mineral salt comprises about 5% to about 75% by weight, and the ratio of the weight of the gel-forming fiber to the weight of the drug or therapeutic agent is between about 1,000:0.5 and 1:1.5.

3. The composition of claim 1, wherein the gel-forming dietary fiber comprises about 50% by weight of the composition.

4. The composition of claim 1, wherein the mineral salt comprises about 15% by weight of the composition.

5. The composition of claim wherein the mineral carbonate or bicarbonate is selected from the group consisting of calcium carbonate, magnesium carbonate, magnesium bicarbonate, sodium carbonate, sodium bicarbonate, potassium carbonate and potassium bicarbonate.

6. The composition of claim 1, wherein the gel-forming dietary fiber comprises about 50% by weight and the mineral comprises about 15% by weight, and the ratio of the weight of the gel-forming fiber to the weight of the drug or therapeutic agent is between about 1,000:0.5 and 1:1.5.

7. A solid prolonged-release oral unit dosage composition for oral administration and ingestion in solid form, and intended to be swallowed as such, which consists essentially of a solid admixture of an effective dose of a biologically-absorbable therapeutic agent or drug, a gel-forming dietary fiber, a mineral salt which releases a physiologically-acceptable gas upon ingestion, and a soluble sugar, the combination of the fiber and salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the mineral salt comprises about 5% to about 75% by weight, and the soluble sugar comprises about 1% to about 30% by weight, and the ratio of the weight of the gel-forming fiber to the weight of the drug or therapeutic agent is between about 1,000:0 5 and 1:1.5.

8. The composition of claim 7, wherein the soluble sugar is present in an amount between about 3% and about 12% by weight of the composition.

9. The composition of claim 1, wherein the drug or therapeutic agent is niacin.

10. A method for prolonging the release of a drug or active therapeutic agent upon oral ingestion by a human being, comprising the step of orally administering to said human being a prolonged-release unit dosage oral composition in solid form which consists essentially of a solid admixture of an effective dose of a biologically-absorbable drug or therapeutic agent, a gel-forming dietary fiber, and a mineral salt which releases a physiologically-acceptable gas upon ingestion, the combination of the fiber and salt providing amounts thereof, which effect prolonged but effective release of the drug or therapeutic agent upon oral ingestion and exposure of the solid composition of biological fluids.

11. The method of claim 10, wherein the mineral salt is selected from the group consisting of calcium carbonate, magnesium carbonate, magnesium bicarbonate, sodium carbonate, sodium bicarbonate, potassium carbonate, and potassium bicarbonate.

12. The method of claim 10, wherein the gel-forming dietary fiber comprises about 10% to about 85% by weight, the mineral salt comprises about 5% to about 75% by weight, and the ratio of the weight of the gel-forming fiber to the weight of the drug or therapeutic agent is between about 1,000:0.5 and 1:1.5.

13. The method of claim 10, wherein the gel-forming dietary fiber comprises about 50% by weight of the composition.

14. The method of claim 10, wherein the mineral salt comprises about 15% by weight of the composition.

15. The method of claim 10, wherein the gel-forming dietary fiber comprises about 50% by weight, the mineral salt comprises about 15% by weight, and the ratio of the weight of gel-forming fiber to the weight of the drug or therapeutic agent is between about 1,000:0.5 and 1:1.5.

16. A method for prolonging the release of a drug or active therapeutic agent upon oral ingestion by a human being, comprising the step of orally administering to said human being a prolonged-release unit dosage oral composition in solid form which consists essentially of a solid admixture of an effective dose of a biologically-absorbable drug or therapeutic agent, a gel-forming dietary fiber, a mineral salt which releases a physiologically-acceptable gas upon ingestion, and a soluble sugar, the combination of the fiber and salt providing amounts thereof which effect prolonged but effective release of the drug or therapeutic agent upon oral ingestion and exposure of the composition to biological fluids wherein the gel-forming dietary fiber comprises about 10% to about 85% by weight, the mineral salt comprises about 5% to about 75% by weight, and the soluble sugar comprises about 1% and about 30% by weight, and the ratio of the weight of the gel-forming fiber to the weight of the drug or therapeutic agent is between about 1,000:0.5 and 1:1.5.

17. The method of claim 16, wherein the soluble sugar is present in an amount between 3% and about 12% by weight of the composition.

18. The method of claim 10, wherein the drug or therapeutic agent is niacin.

19. A solid prolonged-release oral unit dosage composition for oral administration and ingestion in solid form, and intended to be swallowed as such, which consists essentially of a solid admixture of an effective dose of a biologically-absorbable therapeutic agent or drug, a gel-forming dietary fiber, a physiologically-acceptable acid, and a mineral salt which releases a physiologically-acceptable gas upon ingestion, wherein the acid comprises up to about 50% by weight of the composition and wherein the combination of the fiber, acid, and salt provides prolonged but effective release of the drug or therapeutic agent upon oral ingestion and exposure of the solid composition to biological fluids.

20. The composition of claim 19, wherein the gas released is carbon dioxide.

21. The composition of claim 20, wherein the mineral salt is a mineral carbonate or bicarbonate.

22. The composition of claim 21, wherein the mineral salt is selected from the group consisting of calcium carbonate, magnesium carbonate, magnesium bicarbonate, sodium carbonate, sodium bicarbonate, potassium carbonate, and potassium bicarbonate.

23. The composition of claim 19, wherein the acid is a food-grade organic acid or phosphoric acid.

24. A solid prolonged-release oral unit dosage composition for oral administration and ingestion in solid form, and intended to be swallowed as such, which consists essentially of a solid admixture of an effective dose of a biologically-absorbable therapeutic agent or drug, a gel-forming dietary fiber, a physiologically-acceptable acid, a mineral salt which releases a physiologically-acceptable gas upon ingestion, and a soluble sugar, the combination of the fiber, acid and salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the physiologically-acceptable acid comprises up to about 50% by weight, the mineral salt comprises about 5% to about 75% by weight, and the ratio of the weight of the gel-forming fiber to the weight of the drug or therapeutic agent is between about 1,000:0.5 and 1:1.5.

25. The composition of claim 19, wherein the gel-forming dietary fiber comprises about 50% by weight of the composition.

26. The composition of claim 19, wherein the physiologically-acceptable acid comprises about 5% by weight of the composition.

27. The composition of claim 19, wherein the mineral salt comprises about 15% by weight of the composition.

28. The composition of claim 19, wherein the gel-forming dietary fiber comprises about 50% by weight, the physiologically-acceptable acid comprises about 5% by weight, the mineral salt comprises about 15% by weight, and the ratio of the weight of the gel-forming fiber to the weight of the drug or therapeutic agent is between about 1,000:0.5 and 1:1.5.

29. A solid prolonged-release oral unit dosage composition for oral administration and ingestion in solid form, and intended to be swallowed as such, which consists essentially of a solid admixture of an effective dose of a biologically-absorbable therapeutic agent or drug, a gel-forming dietary fiber, a physiologically-acceptable acid, a mineral salt which releases a physiologically-acceptable gas upon ingestion, and a soluble sugar in an amount between about 1% and about 30% by weight of the composition, the combination of the fiber, acid and salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the physiologically-acceptable acid comprises up to about 50% by weight, the mineral salt comprises about 5% to about 75% by weight, and the ratio of the weight of the gel-forming fiber to the weight of the drug or therapeutic agent is between about 1,000:0.5 and 1:1.5.

30. The composition of claim 29, wherein the soluble sugar is present in an amount between about 3% and about 12% by weight of the composition.

31. The composition of claim 19, wherein the drug or therapeutic agent is niacin.

32. A solid prolonged-release oral unit dosage composition for oral administration and ingestion in solid form, and intended to be swallowed as such, which consists essentially of a solid admixture of an effective dose of a biologically-absorbable therapeutic agent or drug, a gel-forming dietary fiber, a physiologically-acceptable acid, and a mineral salt which releases a physiologically-acceptable gas upon ingestion, wherein the drug or therapeutic agent is niacin in granular form, with a cellulose coating about the granules thereof, the combination of the fiber, acid, and salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the physiologically acceptable acid comprises up to about 50% by weight, the mineral salt comprises about 5% to about 75% by weight, and the ratio of the weight of the gel-forming fiber to the weight of the drug or therapeutic agent is between about 1,000:0.5 and 1:1.5.

33. The composition of claim 31, wherein the niacin is present in an amount between about 100 and about 200 mg/per unit dosage form.

34. The composition of claim 33, in tablet form.

35. A prolonged-release unit dosage formulation or composition consisting essentially of an effective dose of niacin, a gel-forming dietary fiber in an amount between about 10% to about 85% by weight of the composition, a physiologically-acceptable acid in an amount between 0% and about 50% by weight of the composition, and a mineral salt which releases a physiologically-acceptable gas upon ingestion in an amount of between about 5% and about 75% by weight.

36. The composition of claim 35, in tablet form.

37. The composition of claim 36, wherein the amount of the niacin is between about 100 mg and about 200 mg per tablet.

38. A prolonged-release unit dosage composition consisting essentially of an effective dose of niacin, in granular form, the granules being coated with a cellulose coating, a gel-forming dietary fiber in an amount of about 10% to about 85% by weight of the composition, a physiologically-acceptable acid in an amount of up to about 50% by weight of the composition, and a mineral salt which releases a physiologically-acceptable gas upon ingestion in an amount of about 5% to about 75% by weight, and wherein the ratio of the weight of the gel-forming fiber to the niacin is between about 1,000:0.5 and about 1:1.5.

39. The composition of claim 38, wherein the coating is a combination of a carboxymethylcellulose coating and an ethylcellulose coating.

40. The composition of claim 35, wherein the gel-forming fiber is psyllium husk powder or guar gum.

41. The composition of claim 35, wherein the mineral salt is a carbonate or bicarbonate.

42. The composition of claim 41, wherein the mineral salt is calcium carbonate.

43. A method for prolonging the release of a drug or active therapeutic agent upon oral ingestion by a human being, comprising the step of orally administering to said human being a prolonged-release unit dosage oral composition in solid form which consists essentially of a solid admixture of an effective dose of a biologically-absorbable drug or therapeutic agent, a gel-forming dietary fiber, a physiologically acceptable acid comprising up to about 50% by weight of the composition, and a mineral salt which releases a physiologically-acceptable gas upon ingestion, the combination of the fiber, acid, and salt providing amounts thereof, which effect prolonged but effective release of the drug or therapeutic agent upon oral ingestion and exposure of the solid composition to biological fluids.

44. The method of claim 43, wherein the gas released is carbon dioxide.

45. The method of claim 44, wherein the mineral salt is a mineral carbonate or bicarbonate.

46. The method of claim 45, wherein the mineral salt is selected from the group consisting of calcium carbonate, magnesium carbonate, magnesium bicarbonate, sodium carbonate, sodium bicarbonate, potassium carbonate, and potassium bicarbonate.

47. The method of claim 43, wherein the physiologically-acceptable acid is a food-grade organic acid or phosphoric acid.

48. A method for prolonging the release of a drug or active therapeutic agent upon oral ingestion by a human being, comprising the step of orally administering to said human being a prolonged-release unit dosage oral composition in solid form which consists essentially of a solid admixture of an effective dose of a biologically-absorbable drug or therapeutic agent, a gel-forming dietary fiber, a physiologically-acceptable acid, a mineral salt which releases a physiologically-acceptable gas upon ingestion, and a soluble sugar, the combination of the fiber, acid and salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the physiologically-acceptable acid comprises up to 50% by weight, the mineral salt comprises about 5% to about 75% by weight, and the ratio of the weight of the gel-forming fiber to the weight of the drug or therapeutic agent is between about 1,000:0.5 and 1:1.5.

49. The method of claim 43, wherein the gel-forming dietary fiber comprises about 50% by weight of the composition.

50. The method of claim 43, wherein the mineral salt comprises about 15% by weight of the composition.

51. The method of claim 10, wherein the gas released is carbon dioxide.

52. The method of claim 10, wherein the gel forming dietary fiber comprises about 50% by weight, the mineral salt comprises about 15% by weight, the gas released is carbon dioxide, and the ratio of the weight of gel-forming fiber to the weight of the drug or therapeutic agent is between about 1,000:05 and 1:1.5.

53. A method for prolonging the release of a drug or active therapeutic agent upon oral ingestion by a human being, comprising the step of orally administering to said human being a prolonged-release unit dosage oral composition in solid form which consists essentially of a solid admixture of an effective dose of a biologically-absorbable drug or therapeutic agent, a gel-forming dietary fiber, a physiologically-acceptable acid, and a mineral salt which releases a physiologically-acceptable gas upon ingestion, and a soluble sugar in an amount between about 1% and about 30% by weight of the composition, the combination of the fiber, acid and salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the physiologically-acceptable acid comprises up to about 50% by weight, the mineral salt comprises about 5% to about 75% by weight, and the ratio of the weight of the gel-forming fiber to the weight of the drug or therapeutic agent is between about 1,000:0.5 and 1:1.5.

54. The method of claim 53, wherein the soluble sugar is present in an amount between about 3% and about 12% by weight of the composition.

55. A method for prolonging the release of a drug or active therapeutic agent upon oral ingestion by a human being, comprising the step of orally administering to said human being a prolonged-release unit dosage oral composition in solid form which consists essentially of a solid admixture of an effective dose of a biologically-absorbable drug or other therapeutic agent, a gel-forming dietary fiber, a physiologically-acceptable acid, a mineral salt which releases a physiologically-acceptable gas upon ingestion, and between about 1% and about 30% by weight of a soluble sugar, wherein the gel-forming dietary fiber comprises about 50% by weight, the physiologically-acceptable acid comprises up to about 50% by weight, the mineral salt comprises about 15% by weight, and the ratio of the weight of gel-forming fiber to the weight of the drug or therapeutic agent is between about 1,000:0.5 and 1:1.5, the combination of the fiber, acid and salt providing amounts thereof which effect prolonged but effective release of the drug or therapeutic agent upon oral ingestion and exposure of the solid composition to biological fluids.

56. The method of claim 43, wherein the drug or therapeutic agent is niacin.

57. A method for prolonging the release of a drug or active therapeutic agent upon oral ingestion by a human being, comprising the step of orally administering to the said human being a prolonged-release unit dosage oral composition in solid form which consists essentially of a solid admixture of an effective dose of a biologically-absorbable drug or therapeutic agent, a gel-forming dietary fiber, a physiologically-acceptable acid, and a mineral salt which releases a physiologically-acceptable gas upon ingestion, wherein the drug or therapeutic agent is niacin in granular form, with a cellulose coating about the granules thereof, the combination of the fiber, acid and salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the physiologically-acceptable acid comprises up to about 50% by weight, the mineral salt comprises about 5% to about 75% by weight, and the ratio of the weight of the gel-forming fiber to the weight of the drug or therapeutic agent is between about 1,000:0.5 and 1:1.5.

58. The method of claim 56, wherein the niacin is present in an amount between about 100 and about 200 mg/per unit dosage form.

59. The method of claim 58, wherein the dosage unit is a tablet.

60. A method for prolonged release of a drug or active therapeutic agent upon administration to a human being comprising the step of administering to the said human being a composition which consists essentially of an effective dose of niacin, a gel-forming dietary fiber in an amount of about 10% to about 85% by weight of the composition, a physiologically-acceptable acid in an amount of up to about 50% by weight of the composition and a mineral salt which releases a physiologically-acceptable gas upon ingestion in an amount of between about 5% and about 75% by weight.

61. The method of claim 60, wherein the dosage unit is a tablet.

62. The method of claim 61, wherein the amount of the niacin is between about 100 mg and about 200 mg per tablet.

63. A method for prolonged release of a drug or active therapeutic agent upon administration to a human being, comprising the step of administering to said human being a prolonged-release unit dosage composition which consists essentially of an effective dose of niacin in granular form, the granules being coated with a cellulose coating, a gel-forming dietary fiber in an amount of about 10% to about 85% by weight of the composition, a physiologically-acceptable acid in an amount of up to about 50% by weight of the composition, and a mineral salt which releases a physiologically-acceptable gas upon ingestion in an amount of about 5% to about 75% by weight, and wherein the ratio of the weight of the gel-forming fiber to the niacin is between about 1,000:0.5 and about 1:1.5.

64. The method of claim 63, wherein the coating is a combination of a carboxymethylcellulose coating and an ethylcellulose coating.

65. The method of claim 60, wherein the gel-forming fiber is psyllium husk powder or guar gum.

66. The method of claim 60, wherein the mineral salt is a carbonate or bicarbonate.

67. The method of claim 66, wherein the mineral salt is calcium carbonate.

68. The composition of claim 35, wherein the drug or therapeutic agent is selected from the group consisting of an analgesic, an antihypercholesterolemic, a vitamin, a stimulant, an appetite suppressant, and a mineral supplement.

69. The method of claim 60, wherein the drug or therapeutic agent is selected from the group consisting of an analgesic, an antihypercholesterolemic, a vitamin, a stimulant, an appetite suppressant and a mineral supplement.

* * * * *